US00PP19046P2

(12) United States Plant Patent
Lim

(10) Patent No.: US PP19,046 P2
(45) Date of Patent: Jul. 22, 2008

(54) SHRUB ROSE PLANT NAMED 'BAILOAD'

(50) Latin Name: *Rosa hybrida*
Varietal Denomination: BAIload

(75) Inventor: Peter P. Lim, McMinnville, OR (US)

(73) Assignee: Bailey Nurseries, Inc, Newport, MN (US)

( * ) Notice: Subject to any disclaimer, the term of this patent is extended or adjusted under 35 U.S.C. 154(b) by 0 days.

(21) Appl. No.: 11/809,232

(22) Filed: May 31, 2007

(51) Int. Cl.
*A01H 5/00* (2006.01)

(52) U.S. Cl. ..... Plt./104

(58) Field of Classification Search ..... Plt./104
See application file for complete search history.

*Primary Examiner*—Kent L. Bell
(74) *Attorney, Agent, or Firm*—Penny J. Aguirre

(57) ABSTRACT

A new cultivar of shrub rose, *Rosa* 'BAIload', characterized by its fully double, deep yellow fragrant flowers that mature to a creamy yellow, its upright and compact plant habit and is everblooming. The new variety has medium green foliage that is resistant to black spot and powdery mildew, is readily propagated on its own roots and is hardy in U.S.D.A. Zones 5 to 9.

2 Drawing Sheets

Botanical classification: *Rosa hybrida.*
Variety denomination: 'BAIload'.

BACKGROUND OF THE INVENTION

The present invention relates to a new and distinct cultivar of *Rosa hybrida.* The new cultivar will be referred to hereafter by its cultivar name, 'BAIload'. 'BAIload' is a shrub rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAIload', designated as seedling No 97RMX1 was selected among seedlings derived from a cross made in Yamhill, Oreg. in 1991 between the female parent, 'RADsun' (U.S. Plant Pat. No. 13,063) and the male parent, an unnamed intermediate seedling derived from a cross between 'RADsun' as the female parent and 'Noason' (not patented) as the male parent. 'BAIload' was selected as unique and budded onto understock in August 1998 and reselected by the inventors for its distinct characteristics in 2001.

The new cultivar has been asexually propagated by rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of six years in Yamhill, Oreg. and evaluated further at several other test sites in the U.S. These attributes in combination distinguish 'BAIload' as a unique cultivar of shrub rose.

1. 'BAIload' exhibits fully double deep yellow colored flowers that change to a creamy yellow color as they mature. Classified as deep yellow by American Rose Society standards.
2. 'BAIload' exhibits an upright, compact plant habit.
3. 'BAIload' exhibits medium green foliage.
4. 'BAIload' is everblooming.
5. 'BAIload' has shown excellent resistance to rose blackspot (*Diplocarpon rosae*) and powdery mildew (*Sphaerotheca pannosa* var. *rosa*).
6. 'BAIload' is very fragrant.
7. 'BAIload' is hardy in U.S.D.A. Zones 5 to 9.
8. 'BAIload' is a vigorous grower and readily propagated by softwood cuttings and grown on its own roots.

The new cultivar of shrub rose can be readily distinguished from its parents and other cultivars. The female parent, 'RADsun', has flowers that are light yellow in color with one third less petals and that lack fragrance. The male component of the male parent, 'Noason', has lighter yellow, semi-double flowers. The cultivars 'AUSmas' (not patented) and 'JACyelsh' (U.S. Plant Pat. No. 10,823) are the closest comparison roses. They both have similarity to 'BAIload' in flower color and have upright plant habits, however they are both taller in height. They also differ in that 'AUSmas' has orange to gold flower buds, pale green foliage and is a recurrent bloomer while 'JACyelsh' has double flowers that are not as full, lighter green foliage and flowers that mature to a medium yellow color rather than creamy yellow.

BRIEF DESCRIPTION OF THE DRAWING

The accompanying colored photographs illustrate the overall appearance and distinct characteristics of the new shrub rose, 'BAIload', as grown outdoors in trial blocks and containers in St. Paul, Minn. and Yamhill, Oreg. The photographs were taken of two to three year-old plants grown on their own roots.

Figure 1:
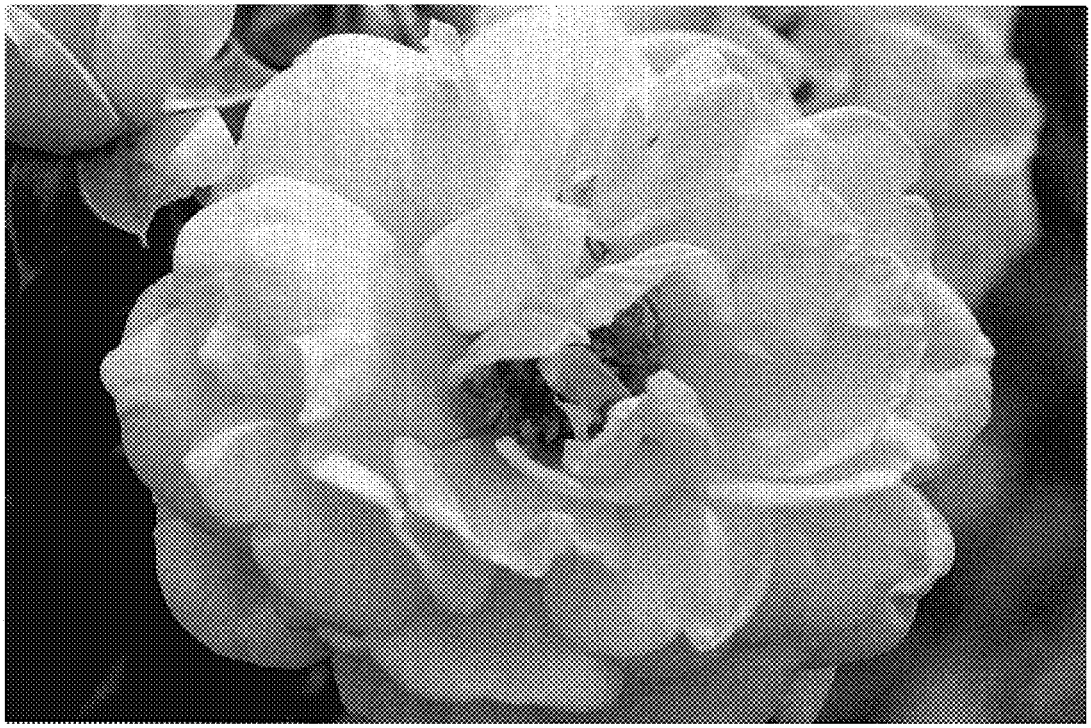
FIG. 1 provides a view of a fully open flower.
Figure 2:
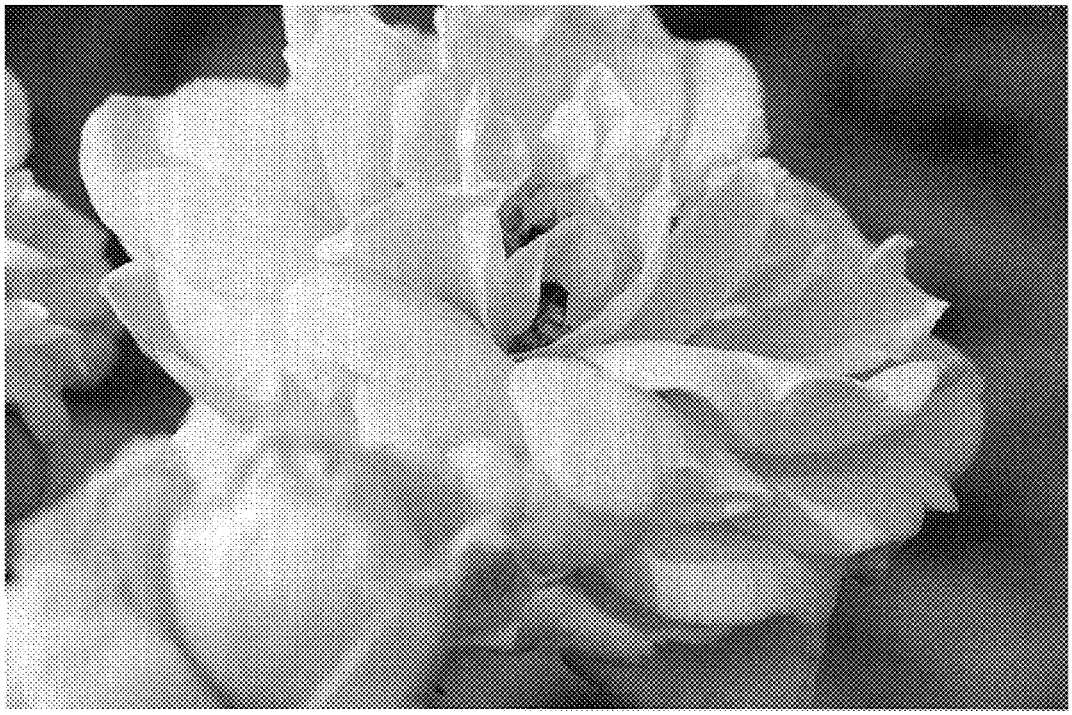
FIG. 2 provides a view of a flower bud just prior to opening and a nearly fully open flower.
Figure 3:
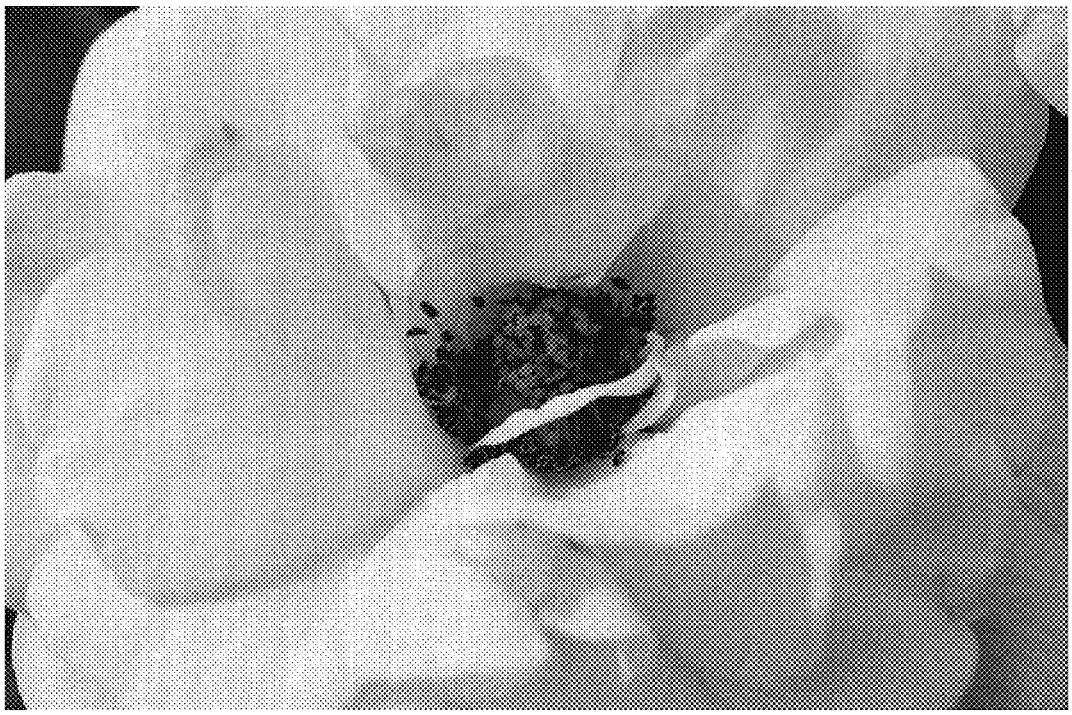
FIG. 3 provides a view of a mature flower.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two year-old container plants and six year-old field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Rosa hybrida* 'BAIload'.

*Blooming habit.*—Everblooming throughout the growing season.

*Plant habit.*—Upright.

*Height and spread.*—Reaches 60 to 125 cm in height and 60 to 125 cm in spread.

*Cold hardiness.*—U.S.D.A. Zone 5 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young and maturing: between 138A and 138B, mature wood; 197A with areas of 138A showing through ridges.

*Stem surface.*—Young and mature; glabrous with sparse sharp prickles 155A in color, adult wood; mostly glabrous with bark-like ridges.

*Stem size.*—Average of 3 mm in width and up to 40 cm in length.

*Thorns.*—Narrowly triangular in shape and horizontal to slightly curved downward, oval base, average of 4 per 5 cm in number, average of 9 mm in length with a base 5 mm in length and 2 mm in width, color 144B to 144D.

Foliage description:

*Leaves.*—Division is odd-pinnate, arrangement is alternate, average of 9 cm in length and 6.5 cm in width, internode length is an average of 2 cm.

*Leaflets.*—5 to 7, oval in shape, cuneate base, acute to acuminate apex, finely serrated margins, glabrous and dull on upper surface and finely pubescent on lower surface, average of 3.5 cm in length and 1.5 cm in width, color: young leaves upper and lower surface; 144A, mature leaves upper surface; 137A, mature leaves lower surface; 137C, pinnately veined (not conspicuous).

*Rachis.*—Average of 4.5 cm in length and 1.3 mm in diameter, color of upper surface 144A, color of lower surface 144C, surface is lightly pubescent with small prickles on underside (about 3 per rachis).

*Stipules.*—Parallel with auricle facing outward, average of 1.2 cm in length and 4 mm in width, color; upper side 144A with 144D on middle ridge, lower surface 144A.

*Petioles.*—Average of 1 cm in length and 1.2 mm in diameter, color of upper surface 144A, color of lower surface 144C, slightly pubescent surface.

Inflorescence description:

*Inflorescence type.*—Single terminal double flowers or in corymbs of 2 to 3 flowers.

*Flower number.*—Average of 1 per lateral stem, about 12 per 2 gallon plant.

*Flower fragrance.*—Strong rose scent.

*Flower longevity.*—About 3 to 5 days, depending on temperature and sunlight exposure.

*Flower type.*—Full (fully double).

*Flower size.*—5 to 7 cm in diameter and 3 cm in depth.

*Peduncles.*—Stiff, average of 3.5 cm in length and 2 mm in diameter, glabrous, color is 144A.

*Bracts.*—Average of 2 per flower, average of 2.5 cm in length and 3 mm in width, lanceolate in shape, ciliate margins, acuminate to leaf-like apex, and truncate base, sessile, color of upper surface 144A and 137A near apex and 144C near center, color of lower surface 137A with 144C in center near base.

*Flower buds.*—Ovate in shape, medium in size with an average of 1.8 cm in length and 1.6 cm in width prior to opening, color 7A.

*Sepals.*—5, broadly lanceolate in shape, margin is entire and ciliate with 3 having foliaceous appendages in a pinnate pattern, color of upper surface 191A, color of lower surface 138A, upper surface is 138C and canascent with white tint due to short white hairs, lower surface glabrous, average of 2 cm in length and 8 mm in width, apex is apiculate to a small leaf, base is truncate, aspect is upright in tight bud stage changing to reflexed prior to flower opening.

*Petals.*—About 38, drop readily and cleanly, orbicular to obovate in shape and curled under on sides, upper and lower surface is glabrous and satiny, entire margin, cuneate base, apex is rounded to cordate, average of 2 cm in length and 1.6 cm in width, color: opening flowers upper and lower surface; 7A to 7B, fully open flowers upper and lower surface; 7A to 7B blending to 4C towards apex, mature flowers fade to 155D with markings of 4D, particularly near base, base petal spot; none.

*Receptacle.*—Average of 7 mm in diameter and 6 cm in depth when flower is fully open, bell shaped, glabrous and satiny, color is 144A blended with 144B.

*Pistils.*—About 20, stigma is an average of 0.5 mm in length, an average of 1 mm in width and 1C in color, style is an average of 6 mm in length and 154D in color towards the base and 63A in color towards apex.

*Stamens.*—About 60, appear deformed, filaments are about 7 mm in length and 162B in color, anthers are an average of 1.1 mm in length, an average of 1 mm in width and 162B in color, pollen is 165B in color.

*Hips.*—Round in shape, yellow orange in color.

I claim:

1. A new and distinct cultivar of shrub rose plant named 'BAIload' as herein illustrated and described.

* * * * *